(12) United States Patent
Gallet et al.

(10) Patent No.: US 6,987,106 B1
(45) Date of Patent: Jan. 17, 2006

(54) 1,4-DIAZABICYCLO[3.2.2]NONANE-4-CARBOXYLATES AND CARBOXAMIDE DERIVATES, PRODUCTION AND USE THEREOF IN THERAPEUTICS

(75) Inventors: Thierry Gallet, Palaiseau (FR); Samir Jegham, Montferrier sur Lez (FR); Patrick Lardenois, Bourg la Reine (FR); Alistair Lochead, Charenton (FR); Alain Nedelec, Colombes (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 09/937,045

(22) PCT Filed: Mar. 21, 2000

(86) PCT No.: PCT/FR00/00697

§ 371 (c)(1),
(2), (4) Date: Sep. 20, 2001

(87) PCT Pub. No.: WO00/58311

PCT Pub. Date: Oct. 5, 2000

(30) Foreign Application Priority Data

Mar. 30, 1999 (FR) .................................. 99 03934

(51) Int. Cl.
*A61P 25/00* (2006.01)
*A61K 31/551* (2006.01)
*C07D 471/08* (2006.01)

(52) U.S. Cl. ....................... 514/219; 514/221; 540/556
(58) Field of Classification Search ................. 514/219, 514/221; 540/556
See application file for complete search history.

(56) References Cited

FOREIGN PATENT DOCUMENTS

EP           235878           9/1987

OTHER PUBLICATIONS

B. R. DeCosta et al., J. Medicinal Chemistry, vol. 36, No. 16, pp. 2311-2320, (1993).

*Primary Examiner*—Brenda Coleman

(74) *Attorney, Agent, or Firm*—Balaram Gupta

(57) ABSTRACT

Compounds of general formula

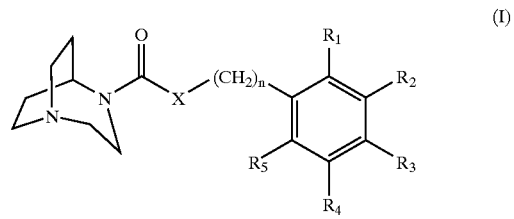

(I)

in which X represents an oxygen atom or a group of formula NZ in which Z represents a hydrogen atom or an alkyl group, n represents a number 0, 1 or 2, and $R_1$, $R_2$, $R_3$, $R_4$ and $R_5$ each represent a hydrogen or halogen atom or a trifluoromethyl, trifluoromethoxy, cyano, hydroxyl, alkyl, alkoxy, phenoxy or phenyl group optionally substituted with a halogen atom or a trifluoromethyl, cyano, hydroxyl, alkyl or alkoxy group, or alternatively $R_2$ and $R_3$ together form a group of formula —$OCH_2O$— or —$CH_2CH_2CH_2CH_2$—.
Application in therapy.

6 Claims, No Drawings

1,4-DIAZABICYCLO[3.2.2]NONANE-4-CARBOXYLATES AND CARBOXAMIDE DERIVATES, PRODUCTION AND USE THEREOF IN THERAPEUTICS

CROSS REFERENCE TO RELATED APPLICATIONS

This application is a 35 U.S.C. §371 application of PCT International application No. PCT/FR00/00697, filed Mar. 21, 2000.

The subject of the present invention is compounds of general formula (I)

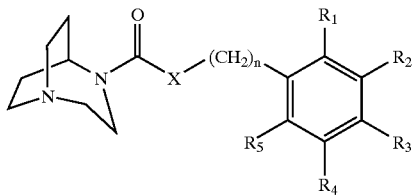

in which

X represents an oxygen atom or a group of formula NZ in which Z represents a hydrogen atom or a $(C_1–C_6)$alkyl group, n represents a number 0, 1 or 2, and $R_1, R_2, R_3, R_4$ and $R_5$ each represent, independently of each other, a hydrogen or halogen atom or a trifluoromethyl, trifluoromethoxy, cyano, hydroxyl, $(C_1–C_6)$ alkyl, $(C_1–C_6)$ alkoxy, phenoxy or phenyl group optionally substituted with a halogen atom or a trifluoromethyl, cyano, hydroxyl, $(C_1–C_6)$alkyl or $(C_1–C_6)$alkoxy group, or alternatively $R_2$ and $R_3$ together form a group of formula —OCH$_2$O— or —CH$_2$CH$_2$CH$_2$CH$_2$—.

The compounds of the invention may exist in the form of bases or of addition salts with acids.

To prepare the compounds of general formula (I), 1,4-diazabicyclo[3.2.2]nonane may be reacted with a compound of general formula (II)

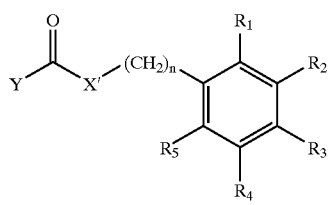

in which n, $R_1, R_2, R_3' R_4$ and $R_5$ are as defined above, X' represents an oxygen atom or a group of formula N-alkyl and Y represents a halogen atom, in the presence of a base such as triethylamine or pyridine.

To prepare the compounds of general formula (I) in which X represents an NH group, it is possible to react 1,4-diazabicyclo[3.2.2]nonane with an isocyanate of general formula (III)

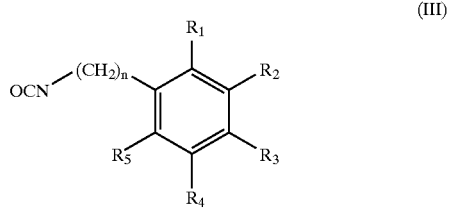

in which n, $R_1, R_2, R_3, R_4$ and $R_5$ are as defined above, under conditions identical to those described above.

1,4-Diazabicyclo[3.2.2]nonane is described in *J. Med. Chem.* (1993) 36 2311–2320.

The compounds of general formulae (II) and (III) are commercially available or may be prepared according to any known methods.

The examples which follow illustrate the preparation of a few compounds of the invention. The elemental microanalyses, and the IR and NMR spectra confirm the structures of the compounds obtained. The numbers indicated in brackets in the titles of the examples correspond to those of the 1$^{st}$ column of the table given later.

In the names of the compounds, the hyphen "-" is part of the word, and the underscore "_" serves only for the break at the end of the line; it should be removed in the absence of a break, and should not be replaced either by a normal hyphen or by a space.

EXAMPLE 1

Compound No. 2

4-Bromophenyl 1,4-diazabicyclo[3.2.2]nonane-4-carboxylate.

0.379 g (3.0 mmol) of 1,4-diazabicyclo[3.2.2]nonane and 0.84 ml (6.0 mmol) of triethylamine in 5 ml of dichloromethane are introduced into a 50-ml three-necked flask, the mixture is cooled to 0° C., 0.730 mg (3.1 mmol) of 4-bromophenyl chloroformate in solution in 3 ml of dichloromethane is added dropwise and the stirring is maintained at 0° C. for 10 min.

The reaction medium is washed with water, the aqueous phase is washed twice with dichloromethane, the combined organic phases are washed with a saturated aqueous sodium chloride solution, dried and the solvent is evaporated off under reduced pressure. The residue obtained is purified by silica gel chromatography, eluting with a 95/5/0.5 mixture of chloroform, methanol and aqueous ammonia. A crude product is obtained which is triturated in diisopropyl ether.

0.77 g of pure product is thus obtained in the form of a white solid.

Melting point 115–116° C.

EXAMPLE 2

Compound No. 8

N-Phenyl-1,4-diazabicyclo[3.2.2]nonane-4-carboxamide hydrobromide (1:1).

0.378 g (3.0 mmol) of 1,4-diazabicyclo[3.2.2]nonane in solution in 10 ml of acetonitrile is introduced into a 25-ml three-necked flask, a solution of 0.358 g (3.0 mmol) of isocyanatobenzene in 2 ml of acetonitrile is added at 3° C. and the reaction medium is stirred for 10 min at room temperature.

The solvent is evaporated off under reduced pressure in order to obtain a solid which is dissolved in 30 ml of ethanol and which is treated with 0.53 ml of a 5.7 M hydrobromic acid solution in acetic acid at 50° C. The precipitate which forms is filtered and it is washed twice with ethanol.

0.649 g of product is thus obtained in the form of a white solid.

Melting point: 229–231° C.

EXAMPLE 3

Compound No. 10

N-Methyl-N-phenyl-1,4-diazabicyclo[3.2.2]nonane-4-carboxamide hydrobromide (1:1).

0.69 ml (1.31 mmol) of a 20% solution of phosgene in toluene diluted by addition of 4 ml of toluene is introduced into a 25-ml three-necked flask (1.31 mmol) and the solution is cooled to 0° C. A solution of 0.127 g (1.12 mmol) of N-methylaniline and 0.11 ml of pyridine in 4 ml of toluene is added over 10 min and the mixture is kept magnetically stirred for 30 min at 0° C.

10 ml of ice-cold water are added and the organic phase is separated. In a 25-ml three-necked flask, this solution is poured over a suspension containing 0.15 g (1.12 mmol) of 1,4-diazabicyclo[3.2.2]nonane in 0.11 ml of pyridine and the mixture is stirred for 30 min.

10 ml of chloroform are added, the solution obtained is washed with 15 ml of a 1 M aqueous sodium hydroxide solution, the solvent is evaporated off and the residue is purified by silica gel chromatography, eluting with a 95/5/0.5 mixture of chloroform, methanol and diethylamine.

0.31 g of product is obtained which is taken up in 5 ml of ethanol, 0.109 ml of an aqueous hydrobromic acid solution is added, the medium is diluted with addition of 5 ml of diisopropyl ether and the precipitate is recovered by filtration.

0.387 g of product is thus obtained in the form of a white solid.

Melting point: 292–293° C.

EXAMPLE 4

Compound No. 11

[1,1'-Biphenyl-4-yl]1,4-diazabicyclo[3.2.2]nonane-4-carboxylate hydrobromide (1:1).

4.1. [1,1'-Biphenyl-4-yl]chloroformate. Preparation according to the method described in *Bull. Soc. Chim. Fr.* (1967).

2.00 g (11.75 mmol) of [1,1'-biphenyl]-4-ol in suspension in 50 ml of dichloromethane are introduced into a 50-ml three-necked flask, 0.47 g (11.75 mmol) of 60% sodium hydride in mineral oil is added portionwise, and the solvent is evaporated off under reduced pressure. A white solid is obtained which is added over 1 h to 6.84 ml (12.92 mmol) of a 20% solution of phosgene in toluene at 30° C. and left in contact for 3 h.

The solvent is evaporated off under reduced pressure, the residue is triturated in petroleum ether, filtered to remove the minerals and the solvent is evaporated off under reduced pressure.

0.89 g of crude product is thus obtained.

Melting point: 36° C.

4.2. [1,1'-Biphenyl-4-yl]1,4-diazabicyclo[3.2.2]nonane-4-carboxylate hydrobromide (1:1).

0.15 g (1.19 mmol) of 1,4-diazabicyclo[3.2.2]nonane and 0.33 ml (2.38 mmol) of triethylamine in solution in 10 ml of chloroform are introduced into a 50-ml three-necked flask, the mixture is cooled to 0° C. and then the chloroformate previously obtained in solution in 10 ml of chloroform is added over 10 min. The mixture is stirred at 0° C. for 10 min before allowing the temperature to rise to ambient temperature and it is left at room temperature for 18 h.

15 ml of 1 M sodium hydroxide are added and the mixture is extracted with chloroform. The solvent is evaporated off under reduced pressure and the residue obtained is purified by silica gel chromatography, eluting with a 98/2/0.2 and then 96/4/0.4 mixture of chloroform, methanol and diethylamine.

0.31 g of product is obtained which is dissolved in 5 ml of ethanol, the solution is treated with 0.109 ml (0.96 mmol) of an aqueous hydrobromic acid solution, 5 ml of diisopropyl ether are added and the precipitate is filtered.

0.387 g of product is thus obtained in the form of a white solid.

Melting point 292–293° C.

The table which follows illustrates the chemical structures and the physical properties of some compounds of the invention.

In the "Salt" column, "-" denotes a compound in the form of a base, "HBr" denotes a hydrobromide and "ox" denotes an oxalate, or ethanedioate; the acid:base molar ratio is indicated adjacent thereto.

TABLE

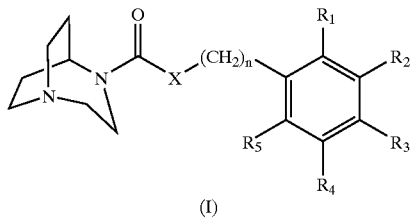

(I)

| No. | X | n | R$_1$ | R$_2$ | R$_3$ | R$_4$ | R$_5$ | Salt | m.p. (° C.) |
|---|---|---|---|---|---|---|---|---|---|
| 1 | O | 0 | H | H | Cl | H | H | — | 109–110 |
| 2 | O | 0 | H | H | Br | H | H | — | 115–116 |
| 3 | O | 0 | H | H | CH$_3$ | H | H | — | 92–93 |
| 4 | O | 0 | H | H | OCH$_3$ | H | H | — | 83.5 |
| 5 | O | 0 | H | H | H | H | H | HBr 1:1 | 239–240 |
| 6 | O | 0 | H | H | NO$_2$ | H | H | — | 98 |
| 7 | O | 0 | H | H | F | H | H | — | 66–68 |
| 8 | NH | 0 | H | H | H | H | H | HBr 1:1 | 229–231 |
| 9 | O | 1 | H | H | H | H | H | HBr 1:1 | 175.5–176 |
| 10 | NCH$_3$ | 0 | H | H | H | H | H | HBr 1:1 | 206–207 |
| 11 | O | 0 | H | H | C$_6$H$_5$ | H | H | HBr 1:1 | 292–293 |
| 12 | O | 0 | Br | H | H | H | H | — | 87–88 |
| 13 | O | 0 | CH$_3$ | H | H | H | H | ox 1:1 | 164–166 |
| 14 | O | 0 | H | CH$_3$ | H | H | H | ox 1:1 | 164–166 |
| 15 | O | 0 | H | OCH$_3$ | H | H | H | ox 1:1 | 152–154 |
| 16 | O | 0 | H | CF$_3$ | H | H | H | ox 1:1 | 95–96 |
| 17 | O | 0 | H | OCH$_2$O | | H | H | — | 123–124 |
| 18 | O | 0 | OCH$_3$ | H | H | H | OCH$_3$ | — | 130–131 |
| 19 | O | 0 | H | F | F | H | H | ox 1:1 | 171–173 |
| 20 | O | 0 | H | Cl | Cl | H | H | ox 1:1 | 174–178 |
| 21 | O | 0 | H | H | OCF$_3$ | H | H | ox 1:1 | 204–205 |
| 22 | O | 0 | H | CH$_2$CH$_2$CH$_2$CH$_2$ | | H | H | ox 1:1 | 202–203 |
| 23 | O | 0 | H | H | OC$_6$H$_5$ | H | H | — | 107–108 |

The compounds of the invention were the subject of trials which demonstrated their therapeutic properties.

The compounds of the invention were also studied in relation to their affinity towards the nicotinic receptors containing the α7 subunit, according to the methods described by Marks and Collins, *J. Pharmacol. Exp. Ther.* (1982) 22 554 and Marks et al., *Mol. Pharmacol.* (1986) 30 427.

150- to 200-g male rats are decapitated, the whole brain is rapidly collected, homogenized with the aid of a Polytron™ grinder in 15 volumes of a 0.32 M sucrose solution, and then it is centrifuged at 1000 g for 10 min. The pellet is removed and the supernatant is centrifuged at 8000 g for 20 min at 4° C. The pellet is recovered and homogenized with the aid of a Polytron™ grinder in 15 volumes of double-distilled water at 4° C., and then it is centrifuged at 8000 g for 20 min. The pellet is removed and the supernatant and the buffy coat are centrifuged at 40,000 g for 20 min. The pellet is recovered, it is resuspended with 15 volumes of double-distilled water at 4° C. and it is again centrifuged once at 40,000 g for 20 min before being stored at −80° C.

On the day of the experiment, the tissue is thawed slowly and it is suspended in 5 volumes of buffer. 150 μl of this membrane suspension are preincubated at 37° C. for 30 min, in the dark, in the presence or absence of the test compound. The membranes are then incubated for 60 min at 37° C., in the dark, in the presence of 50 μl of 1 nM [³H]a-bungarotoxin in a final volume of 250 μl of 20 mM HEPES buffer containing 0.05% of polyethylenimine. The reaction is stopped by filtration on Whatman GF/C™ filters previously treated for 3 hours with 0.5% polyethylenimine. The filters are rinsed with twice 5 ml of buffer at 4° C., and the radioactivity retained on each filter is measured by liquid scintigraphy. The non-specific binding is determined in the presence of α-bungarotoxin at 1 μM final; the non-specific binding represents about 60% of the total binding recovered on the filter. For each concentration of compound studied, the percentage inhibition of the specific binding of [³H]α-bungarotoxin is determined and then the IC$_{50}$, the concentration of compound which inhibits the specific binding by 50%, is calculated.

The IC$_{50}$ values for the compounds of the invention which have the highest affinity are between 0.04 and 0.5 μM.

The results of the preceding trials show that the compounds of the invention are ligands for the α$_7$ subunits of the nicotinic receptor.

These results suggest the use of the compounds in the treatment or prevention of disorders linked to nicotinic receptor dysfunction, in particular at the level of the central nervous system or of the gastrointestinal system.

At the level of the central nervous system, these disorders comprise cognitive impairments, more particularly memory impairments, but also attention impairments, linked to Alzheimer's disease, to pathological ageing (Age Associated Memory Impairment, AAMI), to Parkinson's syndrome, to trisomy 21 (Down's syndrome), to Korsakoff's alcoholic syndrome, to vascular dementia (multi-infarct dementia, MID).

The compounds of the invention could also be useful in the treatment of the motor disorders observed in Parkinson's disease or other neurological diseases such as Huntington's chorea, Tourette's syndrome, tardive dyskinesia and hyperkinesia.

The compounds of the invention may also constitute a curative or symptomatic treatment of cerebrovascular accidents and of cerebral hypoxic episodes.

They may be used in the case of psychiatric pathologies: schizophrenia, depression, anxiety, panic attacks or obsessive-compulsive behaviour.

They can prevent the symptoms due to withdrawal from tobacco, from alcohol and from various substances which induce dependence, such as cocaine, LSD, cannabis, benzodiazepines.

At the level of the gastrointestinal system, the compounds of the invention could be useful in the treatment of Crohn's disease, ulcerative colitis, irritable bowel syndrome and obesity.

To this end, the compounds of the invention may be provided in any forms of compositions appropriate for enteral, parenteral or transdermal administration, such as tablets, sugar-coated tablets, hard gelatine capsules, soft gelatine capsules, oral or injectable suspensions or solutions such as syrups or ampoules, transdermal patches and the like, combined with suitable excipients, and containing doses to allow a daily administration of 0.01 to 20 mg/kg.

What is claimed is:

1. A compound corresponding to the formula (I)

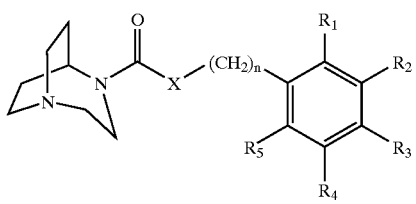

(I)

in which

X represents an oxygen atom or a group of formula NZ in which Z represents a hydrogen atom or a $(C_1–C_6)$alkyl group, n represents a number 0, 1 or 2, and $R_1$, $R_2$, $R_3$, $R_4$ and $R_5$ each represent, independently of each other, a hydrogen or halogen atom or a trifluoromethyl, trifluoromethoxy, cyano, hydroxyl, $(C_1–C_6)$alkyl, $(C_1–C_6)$alkoxy, phenoxy or phenyl group optionally substituted with a halogen atom or a trifluoromethyl, cyano, hydroxyl, $(C_1–C_6)$alkyl or $(C_1–C_6)$alkoxy group, or alternatively $R_2$ and $R_3$ together form a group of formula $OCH_2O$— or —$CH_2CH_2CH_2CH_2$—, in the form of a base or of an addition salt with an acid.

2. A pharmaceutical composition comprising a compound according to claim 1, combined with an excipient.

3. A method for the treatment of Alzheimer's disease or schizophrenia which comprises administering to a patient in need of such treatment an effective amount of a compound according to claim 1.

4. 4-Bromophenyl-1,4-diazabicyclo[3.2.2]nonane-4-carboxylate according to claim 1.

5. A pharmaceutical composition comprising a compound according to claim 4, combined with an excipient.

6. A method for the treatment of Alzheimer's disease or schizophrenia which comprises administering to a patient in need of such treatment an effective amount of a compound according to claim 4.

* * * * *